United States Patent
Yamada

(10) Patent No.: US 6,229,069 B1
(45) Date of Patent: May 8, 2001

(54) METHOD FOR CONTROLLING WATER CONTENT OF PLANT

(75) Inventor: Shigehiro Yamada, Shizuoka-ken (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 09/053,702

(22) Filed: Apr. 2, 1998

Related U.S. Application Data

(63) Continuation of application No. PCT/JP97/03828, filed on Oct. 23, 1997, which is a continuation-in-part of application No. 08/736,287, filed on Oct. 24, 1996, now abandoned.

(51) Int. Cl.$^7$ .............. A01H 4/00; A01H 5/00; C12N 15/29; C12N 15/82
(52) U.S. Cl. .......... 800/298; 800/278; 800/295; 435/419; 435/468; 435/320.1; 536/23.6; 536/24.1
(58) Field of Search ................. 800/278, 295, 800/298; 435/419, 468, 320.1; 536/236, 24.1

(56) References Cited

FOREIGN PATENT DOCUMENTS

WO96/00789 * 1/1996 (WO) .............. C12N/15/82

OTHER PUBLICATIONS

Napoli et al. The Plant Cell, vol. 2, 279–289, Apr. 1990.*
Yamada et al. The Plant Cell, vol. 7, 1129–1142, Aug. 1995.*
Guerrero et al, Plant Molecular Biology, 15:11–26 (1990).
Yamaguchi–Shinozaki et al, Plant Cell Physiol., 33:217–224 (1992).
Kammerloher et al, The Plant Journal, 6(2), pp. 187–199 (1994).
Fray et al, Plant Molecular Biology, 24:539–543 (1994).
Kaldenhoff et al, The Plant Journal, 7(1), pp. 87–95 (1995).
Yamada et al, The Plant Cell, vol. 7, pp. 1129–1142 (1995).
Ludevid et al, Plant Physiol., vol. 100, pp. 1633–1639 (1992).
Höfte et al, The Plant Cell, vol. 4, pp. 995–1004 (1992).
Walz et al, The EMBO Journal, vol. 13, No. 13, pp. 2985–2993 (1994).
Henzler et al, Journal of Experimental Botany, vol. 46, No. 283, pp. 199–209 (1995).
Johnson et al, Plant Physiol., vol. 100, pp. 1787–1795 (1992).
Daniels et al, Plant Physiol., vol. 106, pp. 1325–1333 (1994).
Phillips et al, Plant Molecular Biology, 24:603–615 (1994).
Yamamoto et al, Nucleic Acids Research, vol. 18, No. 24, p. 7449 (1990).
Muramatsu et al, Nucleic Acids Research, vol. 17, No. 11, p. 4378 (1989).
Shiels et al, Nucleic Acids Research, vol. 16, No. 19, p. 9348 (1988).
Sandal et al, Nucleic Acids Research, vol. 16, No. 19, p. 9347 (1988).
Johnson et al, The Plant Cell, vol. 2, pp. 525–532 (1990).
Qi et al, Plant Physiol., 108:387–395 (1995).
Höfte et al, Plant Physiol., vol. 99, pp. 561–570 (1992).
Raina et al, The Journal of Biological Chemistry, vol. 270, No. 4, pp. 1908–1912 (1995).
Daniels et al, The Plant Cell, vol. 8, pp. 587–599 (1996).
Fushimi et al, Nature, vol. 361, pp. 549–553 (1993).
Maurel et al, The EMBO Journal, vol. 12, No.6, pp. 2241–2247 (1993).
Kaldenhoff et al, Plant Molecular Biology, 23:1187–1198 (1993).
Jones et al, Plant Molecular Biology, 28:983–996 (1995).

* cited by examiner

Primary Examiner—Gary Benzion
Assistant Examiner—Thomas Haas
(74) Attorney, Agent, or Firm—Birch, Stewart, Kolasch & Birch, LLP

(57) ABSTRACT

The invention provides a method for controlling the water content of a plant in order to provide a plant which is tolerant to water-related stress. The method is characterized in that a gene encoding a plant water channel protein is operatively introduced into the plant which is desired to be made tolerant to water-related stress.

27 Claims, No Drawings

SEQUENCE LISTING

<160> NUMBER OF SEQ ID NOS: 5

<210> SEQ ID NO 1
<211> LENGTH: 1272
<212> TYPE: DNA
<213> ORGANISM: Mesembryanthemum crystallinum
<220> FEATURE:
<221> NAME/KEY: CDS
<222> LOCATION: (225)..(1070)

<400> SEQUENCE: 1

```
gagagaacta gtctcgagtt ttttttttt tttttttta ttcataagag tttaatgaat      60
aacatacaac aacaacatat ttcacaaatc gaaatttaca gcaatgatgt aattaacctc     120
aactcaaacc accacagtct cacagagcag caccaaaaag agcatagctc actgcctttc     180
tttctagaga gagaaacaag agagagagag aaacaagaga agca atg gag ggg aag      236
                                                Met Glu Gly Lys
                                                  1 gaa gag gat gtg aga cta gga gcc aac aag ttc tcg gag agg cag ccg      284
Glu Glu Asp Val Arg Leu Gly Ala Asn Lys Phe Ser Glu Arg Gln Pro
  5                  10                  15                  20 ctg ggg acg gtg gcg cag gac aga gac tac agg gag cca ccg cgc ggc      332
Leu Gly Thr Val Ala Gln Asp Arg Asp Tyr Arg Glu Pro Pro Arg Gly
                 25                  30                  35 ctc ttt gag gcc ggc gag ctg acg tca tgg tcg ttc tac aga gct ggg      380
Leu Phe Glu Ala Gly Glu Leu Thr Ser Trp Ser Phe Tyr Arg Ala Gly
             40                  45                  50
```

```
att gct gag ttc att gct acc ttc ttg ttc ctc tac atc tct atc ttg      428
Ile Ala Glu Phe Ile Ala Thr Phe Leu Phe Leu Tyr Ile Ser Ile Leu
        55                  60                  65 act gtt atg ggg gtt aat agg agt ccc tca aag tgt gcc agt gtt gga      476
Thr Val Met Gly Val Asn Arg Ser Pro Ser Lys Cys Ala Ser Val Gly
    70                  75                  80 att cag ggt att gct tgg tct ttt ggt ggc atg atc ttt gcc ctt gtt      524
Ile Gln Gly Ile Ala Trp Ser Phe Gly Gly Met Ile Phe Ala Leu Val
85                  90                  95                 100 tac tgc act gct gga att tca gga ggt cac att aac cca gca gtc aca      572
Tyr Cys Thr Ala Gly Ile Ser Gly Gly His Ile Asn Pro Ala Val Thr
                105                 110                 115 ttt ggg cta ttc ttg gca agg aaa ttg tcc ttg aca agg gca gtc ttc      620
Phe Gly Leu Phe Leu Ala Arg Lys Leu Ser Leu Thr Arg Ala Val Phe
            120                 125                 130 tac atg gtc atg caa tgc ttg ggt gcc att tgt ggt gct ggt gtt gtc      668
Tyr Met Val Met Gln Cys Leu Gly Ala Ile Cys Gly Ala Gly Val Val
        135                 140                 145 aag ggc ttc cag cac ccc cta cca gct ctt ggg cgg cgg ggc aac tct      716
Lys Gly Phe Gln His Pro Leu Pro Ala Leu Gly Arg Arg Gly Asn Ser
    150                 155                 160 gtg aac ccc ggc tac acc aag gga tca ggc ctt gcg ctg aga tta tcg      764
Val Asn Pro Gly Tyr Thr Lys Gly Ser Gly Leu Ala Leu Arg Leu Ser
165                 170                 175                 180 gca ctt ttg ttc ttg tct aca ccg tct tct ccg cca ctg acg cca agc      812
Ala Leu Leu Phe Leu Ser Thr Pro Ser Ser Pro Pro Leu Thr Pro Ser
                185                 190                 195 gaa cgt agg gag tcc cat gtt cct atc ttg gct cca ttg cca att ggg      860
Glu Arg Arg Glu Ser His Val Pro Ile Leu Ala Pro Leu Pro Ile Gly
            200                 205                 210 ttc gct gtg ttc ttg gtt cac ttg gcc acc atc ccc gtt act ggc act      908
Phe Ala Val Phe Leu Val His Leu Ala Thr Ile Pro Val Thr Gly Thr
        215                 220                 225 ggc atc aac cca gcc agg agt ctt ggt gct gct atc att tac aac agg      956
Gly Ile Asn Pro Ala Arg Ser Leu Gly Ala Ala Ile Ile Tyr Asn Arg
    230                 235                 240 ccc cat gct tgg gct gac cat tgg att ttc tgg gtg gga ccc ttc atc     1004
Pro His Ala Trp Ala Asp His Trp Ile Phe Trp Val Gly Pro Phe Ile
245                 250                 255                 260 ggt gca gca ctt gca gcc ctg tac cat gta gta gtg ata agg gca att     1052
Gly Ala Ala Leu Ala Ala Leu Tyr His Val Val Val Ile Arg Ala Ile
                265                 270                 275 cca ttc aaa tcc aag tga tgataagatt tcgagtgatg atgaatgatc            1100
Pro Phe Lys Ser Lys
            280 atcggacggc caagattaat tgtcgaggtc tctagatgat aagattggac ccccacgtgt   1160 cattttccct agttattttt atctctcctt ctgtgtttgt cttttgtact gtactagttt   1220 gtaaagttat ggtgttttgg ggtctcagaa gaacgtggga tgtttcatgt tt           1272

<210> SEQ ID NO 2
<211> LENGTH: 281
<212> TYPE: PRT
<213> ORGANISM: Mesembryanthemum crystallinum

<400> SEQUENCE: 2

Met Glu Gly Lys Glu Glu Asp Val Arg Leu Gly Ala Asn Lys Phe Ser
 1               5                  10                  15

Glu Arg Gln Pro Leu Gly Thr Val Ala Gln Asp Arg Asp Tyr Arg Glu
```

```
                  20                  25                  30

Pro Pro Arg Gly Leu Phe Glu Ala Gly Glu Leu Thr Ser Trp Ser Phe
            35                  40                  45

Tyr Arg Ala Gly Ile Ala Glu Phe Ile Ala Thr Phe Leu Phe Leu Tyr
        50                  55                  60

Ile Ser Ile Leu Thr Val Met Gly Val Asn Arg Ser Pro Ser Lys Cys
65                  70                  75                  80

Ala Ser Val Gly Ile Gln Gly Ile Ala Trp Ser Phe Gly Met Ile
                85                  90                  95

Phe Ala Leu Val Tyr Cys Thr Ala Gly Ile Ser Gly Gly His Ile Asn
                100                 105                 110

Pro Ala Val Thr Phe Gly Leu Phe Leu Ala Arg Lys Leu Ser Leu Thr
            115                 120                 125

Arg Ala Val Phe Tyr Met Val Met Gln Cys Leu Gly Ala Ile Cys Gly
        130                 135                 140

Ala Gly Val Val Lys Gly Phe Gln His Pro Leu Pro Ala Leu Gly Arg
145                 150                 155                 160

Arg Gly Asn Ser Val Asn Pro Gly Tyr Thr Lys Gly Ser Gly Leu Ala
                165                 170                 175

Leu Arg Leu Ser Ala Leu Leu Phe Leu Ser Thr Pro Ser Ser Pro Pro
                180                 185                 190

Leu Thr Pro Ser Glu Arg Arg Glu Ser His Val Pro Ile Leu Ala Pro
            195                 200                 205

Leu Pro Ile Gly Phe Ala Val Phe Leu Val His Leu Ala Thr Ile Pro
        210                 215                 220

Val Thr Gly Thr Gly Ile Asn Pro Ala Arg Ser Leu Gly Ala Ala Ile
225                 230                 235                 240

Ile Tyr Asn Arg Pro His Ala Trp Ala Asp His Trp Ile Phe Trp Val
                245                 250                 255

Gly Pro Phe Ile Gly Ala Ala Leu Ala Ala Leu Tyr His Val Val Val
                260                 265                 270

Ile Arg Ala Ile Pro Phe Lys Ser Lys
            275                 280

<210> SEQ ID NO 3
<211> LENGTH: 587
<212> TYPE: DNA
<213> ORGANISM: Nicotiana tabacum

<400> SEQUENCE: 3
gaagatctat gatctttgcc cttgtttact gcactgctgg tatctcagga ggacacatta        60
acccagcagt gacatttggt ctgttttttgg caagaaagtt gtccttaaca agggctctgt      120
tctacatggt gatgcagtgc cttggtgcaa tctgtggtgc tggtgtggtt aaaggtttca      180
tggtgggtcc ataccagaga cttggtggtg gggccaacat ggttcaacct ggctacacaa      240
aaggtgatgg acttggtgct gagattattg gaccttttgt cctagtttac actgttttct      300
ctgccactga tgccaagaga atgctagag attctcatgt ccctatttg gcacctcttc       360 ctattggatt cgcggtgttc ttggttcatt tggccaccat cccaatcacc ggaaccggta      420
tcaaccccgc caggagcctt ggagctgcta tcatcttcaa ccaagaccag gcatgggatg      480
atcactggat cttctgggtt ggaccattca ttggagctgc acttgctgca gtttaccacc      540
agataatcat caggctatt ccattcaagt cgcgtgctag atctgac                     587
```

-continued

```
<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence:Synthetic
      Primer

<400> SEQUENCE: 4
gaagatctat gatctttgcc cttgtttact gc                                  32

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence:Synthetic
      Primer

<400> SEQUENCE: 5
gtcagatcta gcacgcgact tgaatggaat agcc                                34
```

METHOD FOR CONTROLLING WATER CONTENT OF PLANT

This application is a continuation of PCT application no. PCT/JP97/03828 filed on Oct. 23, 1997, which designated the United States and on which priority is claimed under 35 U.S.C. § 120. This application is also a continuation in part of application Ser. No. 08/736,287 filed on Oct. 24, 1996 ABN, the entire contents of which are hereby incorporated by reference.

BACKGROUND OF THE INVENTION

This invention relates to a method for controlling the water content of a plant in order to provide a plant which is tolerant to water-related stress such as salt stress or drought stress.

Plants are continuously exposed to stress even under normal growing conditions. Such stress is caused by various factors such as salt, drought, high temperature, low temperature, strong light, air pollution, etc. From the viewpoint of agriculture, salt and drought stress cause the most serious problems. Salt stress is observed not only in areas which have a soil inherently rich in salt but also in irrigated farms. At present, more than 10% of cultivated land suffers from some degree of salt stress. To increase food production, it is desired to grow crop in land which has previously been regarded as uncultivatable.

Drought stress is caused by unseasonable weather and geographic location. In the United States, drought causes a fall in crop yield once every several years.

Therefore, it is important to find a plant which is tolerant to water-related stress.

In this regard, it is known that water channel proteins (hereinafter sometimes referred to simply as WCH proteins) seemingly have a role to play in "water flux in plants".

These plant WCH proteins are classified into plasma membrane-located types and tonoplast-located types. Some reports have already published on the genes of these proteins.

In connection with the genes of plasma membrane-located WCH proteins, there have been reported, for example, the cloning of cDNA of a turgor responsible WCH protein derived from pea [Plant Molecular Biology 15, 11–26 (1990)]; the cloning of cDNA of a desiccation responsible WCH protein derived from *Arabidopsis thaliana* (Plant Cell Physiology 33, 217–224); WCH gene of *Arabidopsis thaliana* [The Plant Journal 6, 187–199 (1994)]; WCH gene of tomato [Plant Molecular Biology 24, 539–543 (1994)]; the introduction of an antisense gene into *Arabidopsis thaliana* to confirm its function in the water channel [The Plant Journal 7, 87–95 (1995)]; WCH gene of common ice plant (*Mesembryanthemum crystallinum*) [The plant Cell 7, 1129–1142 (1995)], etc. In addition, those derived from corn, rice, kohlrabi (*Brassica oleracea*), soybean, barley, etc. have been registered at gene data bases, etc.

In connection with the genes of tonoplast-located WCH proteins, there have been reported, for example, one derived from tobacco [Nucleic Acids Research 18, 7449 (1990)]; one derived from common bean [The Plant Cell 2, 525–532 (1990)]; one derived from *Arabidopsis thaliana* [Plant Physiology 99, 561–570 (1992)], etc. In addition, those of rice, barley, soybean, radish (*Raphanus sativa*), white clover (*Triforium repens*), alfalfa (*Medicago sativa*), etc. have been registered at gene data bases, etc.

As described above, it has been urgently required to provide a plant which is tolerant to water-related stress. One approach to obtain such a plant is directed to controlling the water content of the plant by, for example, gene manipulation. In general, it is considered that a plant which is tolerant to water-related stress can be obtained by increasing the water content of the plant, namely, enhancing the capability of the plant to obtain water.

To obtain a water-related stress-tolerant plant in the above-mentioned manner, WO 96/00789 and Nature 379 (22) 683–684 (1996) disclose a method for obtaining a plant tolerant to water-related stress by way of controlling the water content of the plant. The method comprises introducing the gene of an enzyme for trehalose biosynthesis into the plant, thereby to induce the synthesis and accumulation of trehalose in the plant, and to eliminate the loss in water content by way of the water-retaining effect of trehalose. The disclosure of these references is incorporated herein by reference.

However, this method suffers from various problems. Namely, a certain amount of carbon fixed by photosynthesis is consumed in this method, which is disadvantageous from the viewpoint of energy consumption. In addition, there is a risk that the accumulation of trehalose might exert adverse effects on the qualities of the product and the metabolic system of the plant.

On the other hand, it has been considered that the WCH proteins described above may participate in water flux in a plant. However, no one has suggested so far that the water content of a plant may be controlled by using these proteins.

SUMMARY OF THE INVENTION

The present invention, which has been accomplished under the above-mentioned circumstances, provides a method for controlling the water content of a plant by introducing a plant WCH protein gene into the plant and aims at thus obtaining a plant tolerant to water related stress.

The present invention further provides a plant which is produced by the above method and hence possesses a controlled water content.

The present invention further provides a plant which has an improved tolerance to drought stress and/or salt stress due to the controlled water content.

DETAILED DESCRIPTION

Now, the present invention will be described in greater detail.

The present invention is characterized in that a plant WCH protein gene is introduced into a plant to thereby control the water content of the plant thus transformed.

The plant WCH proteins to be used in the present invention includes plasma membrane-located WCH proteins and tonoplast-located ones. Although genes encoding proteins of both of these types may be used in the present invention, genes of WCH proteins which are located in plasma membrane are preferred.

As described above, there have been known genes encoding plasma membrane-located WCH proteins of various origins such as pea, *Arabidopsis thaliana*, tomato, *Mesembryanthemum crystallinum*, corn, rice, kohlrabi, soybean, barley, etc. These known genes may be used in the present invention. However, WCH protein genes to be used in the present invention are not limited thereto, provided that those of WCH proteins located in plasma membrane are preferred.

As a method of obtaining a gene of a plasma membrane-located WCH protein, the Examples hereinbelow will illustrate a method to obtain a gene from *Mesembryanthemum*

*crystallinum*. Further, gene from other plants can be obtained by reference to the following literatures.

(1) Pea (*Pisum sativum*) [Plant Molecular Biology 15, 11–26 (1990)].

(2) *Arabidopsis thaliana* [Plant Cell Physiology 33, 217–224 (1992); Plant Molecular Biology 23, 1187–1198 (1993); The Plant Journal 6, 187–199 (1994)].

(3) Tomato [Plant Molecular Biology 24, 539–543 (1994)].

The gene encoding a plant WCH protein to be used in the present invention may be operatively introduced into a plant in such a manner that the genetic code will be translated either in the sense direction or in the antisense direction. In order to enhance the water-retaining capacity of the plant under water stress, it is preferred in the present invention that the gene is introduced into the plant in the sense direction. However, in certain cases, reduced water flux in plants is expected to be beneficial for them and hence, introduction of the gene in the antisense direction will be desired, depending on the strength, timing or kind of stress.

It is preferred in the present invention that the gene encoding a plant WCH protein, which is to be introduced into a plant in the sense direction, is one derived from a plant which is tolerant to salt stress or drought stress, still preferred is one derived from *Mesembryanthemum crystallinum*.

When the gene is introduced into the plant in the antisense direction, on the other hand, it is preferred that the species of the plant to be transformed is as close as possible to the species from which the gene is obtained. It is still preferred that the gene is of the same species as the plant to be transformed. When the gene is introduced in the antisense direction, it is not always necessary to introduce the whole gene. Namely, sufficient effects will be achieved in some cases by using a segment of the gene. Therefore, when the gene is introduced in the antisense direction in the present invention, it is required that at least a portion of the gene is used.

As an expression promoter to be used in the present invention, any known ones may be employed. For example, use can be made of those having intense transcriptional function and being capable of inducing the expression of a gene in any cells (35S, 19S, nos, etc.), those responsive to light (rbc, etc.), those sensitive to temperature (hsp, etc.), those responsive to hormones and those reactive in specific tissues. Of particular preferred is a powerful promoter such as 35S.

In the present invention, it is not necessary to employ any special method for introducing a WCH protein gene into the plant to be transformed either in the sense direction or in the antisense direction. That is, any method commonly employed to transform plants may be used. By way of example, the leaf disk method utilizing bacteria of the genus Agrobacterium will be described herein.

A WCH protein gene is inserted into an appropriate plant expression vector either in the sense direction or in the antisense direction and then the vector is introduced into bacteria belonging to the genus Agrobacterium. Then, leaf disks taken from a germ-free leaf of the plant to be transformed are immersed in a culture medium containing the bacteria. After the formation of calluses, one in which transformation has occurred is selected and grown to thereby give a transformed plant. The selection of transformed plants may be performed, for example, by adding an appropriate antibiotic to the culture medium for callus formation and selecting calluses which are tolerant to the antibiotic. The transformation method utilizing bacteria of the genus Agrobacterium is applicable not only to dicotyledonous plants but also to monocotyledonous plants as disclosed in WO 94/00977 which is incorporated herein by reference.

The plant species to be transformed by the present invention, namely, plants the water content of which is to be controlled by the present invention are not particularly limited. Examples thereof include soybean, corn, potato, tomato, tobacco, etc. Among all, soybean and corn are preferred.

The improved water content of the plant transformed in accordance with the present invention may be determined by various methods. For example, the plant grown to a certain stage is placed under stressful conditions, for example, in a climate chamber, for a certain period of time. Then the aerial part of the plant is harvested and weighed. The plant is subsequently dried at 60° C. for several days and then the dry weight is measured. Thus, the water content may be expressed as the ratio of the fresh weight to the dry weight.

To further illustrate the present invention in greater detail, the following Examples will be given. However, it is to be understood that the present invention is not limited thereto.

EXAMPLE 1

Isolation of the gene of plasma membrane-located WCH protein from *Mesembryanthemum crystallinum*

A total RNA fraction was extracted from a root tissue specimen of *Mesembryanthemum crystallinum* in accordance with the method of Ostrem et al. [Plant Physiology 84, 1270–1275 (1987)], with modifications made as follows:

1) RNA was extracted from the plant which had been subjected to a salt stress-treatment with 400 mM NaCl.

2) The plant was ground and shaken on ice for 1 hour together with the extraction buffer and phenol.

3) After centrifugation, the supernatant was shaken on ice for 1 hour with chloroform.

poly(A)$^+$RNA was purified by the oligo dT cellulose column method. The WCH protein gene was obtained by the differential screening of a cDNA library which was prepared by using the poly(A)$^+$RNA thus purified and ZAP-cDNA synthesis kit in accordance with the manufacturer's instructions. In the differential screening, two different single-stranded DNA were used as probes, namely, one synthesized from the above-mentioned poly(A)$^+$RNA and the other synthesized from poly(A)$^+$RNA isolated and purified in the same manner from a plant not subjected to the salt stress treatment. Thus a plasmid was obtained which contained, the WCH protein gene McMipA of *Mesembryanthemum crystallinum* at the restriction enzyme site EcoRI/XhoI in plasmid pBSK (purchased from STRATAGENE). The nucleotide sequence of this gene encoding the plasma membrane-located WCH protein derived from *Mesembryanthemum crystallinum* and the deduced amino acid sequence are shown respectively in SEQ ID NO:1 and SEQ ID NO:2. In SEQ ID NO:1, the reading frame extends from the start codon ATG at positions 225–227 to the stop codon TGA at positions 1068–1070. The details of differential screening are described in the Plant Cell, 7, 1129–1142, 1995, "A family of transcripts encoding water channel proteins: Tissue-specific expression in the common ice plant" Shigehiro Yamada, Maki Katsuhara, Walter B. Kelly, Cristine B. Michalowski, and Hans J. Bonhert.

EXAMPLE 2

Construction of gene for the transformation of *Nicotiana tabacum*

The plasmid obtained in Example 1, which carried out WCH protein gene McMipA from *Mesembryanthemum crystallinum* at the restriction enzyme site EcoRI/XhoI of plasmid pBSK, was digested with restriction enzyme XbaI to isolate the McMipA gene fragment. This gene fragment was inserted into the XbaI site of binary vector pBI121 (purchased from Clontech) in such a direction by the promoter 35S to thereby give the gene construct pBI4C. The beta-glucuronidase gene contained in pBI121 was deleted with restriction enzymes SmaI and ScaI.

EXAMPLE 3

Transformation of *Nicotiana tabacum*

A green leaf of *Nicotiana tabacum*, which had been aseptically grown in a test tube, was cut into pieces (1 cm·1 cm) and the tissue pieces were immersed in a culture medium (Murashige and Skoog basal medium with Gamborg's vitamins; purchased from SIGMA) in which *Agrobacterium tumefaciens* LBA4404 carrying the gene construct pBI4C obtained in Example 2 was suspended. Then the pieces were left to be infected with *A. tumefaciens* in dark for 2 days. Subsequently, the pieces of tissue were transplanted into an agar medium (the above-mentioned culture medium containing 0.8% of agar) containing antibiotics (100 mg/L of kanamycin and 250 mg/L of cefotaxime) and a plant hormone (0.5 mg/L of 6-benzylaminopurine) and thus redifferentiated plants were obtained. The aerial part of each redifferentiated plant was transplanted into the above-mentioned agar medium containing the antibiotics (100 mg/L of kanamycin and 250 mg/L of cefotaxime) and allowed to root therein. Rooted individuals were transplanted in a closed greenhouse and thus self-pollinated progenies of the transformants were obtained.

EXAMPLE 4

Measurement of change in water content under stressful conditions

Seeds of the transformants obtained in Example 3 were germinated in the above-mentioned agar medium containing 100 mg/L of kanamycin and grown until 2 true leaves developed. Then plants not bleached at this time point were transplanted into pots in a closed greenhouse. After being grown until 4 true leaves developed, the plants were transplanted in a mixture of equivalent amounts of vermiculite and Hydroball and grown in this state for 2 weeks while watering Hoagland's solution (purchased from SIGMA), diluted 4-fold, at a rate of 50 ml/day. Then the plants were transferred into a climate chamber (temperature: 23° C., humidity: 70%, lighting period for 12 hours/dark period for 12 hours). After being grown for several days for acclimation, the stress treatment was performed. The plants in the salt stress group were watered with 100 ml (on the first day) or 50 ml (on the second day and thereafter) of Hoagland's solution (purchased from SIGMA), dilutes 4-fold and containing 250 mM of NaCl. In the drought stress group, watering was suspended. After the end of the experiment period, the aerial part of each plant was harvested and weighed. These plants were then dried at 60° C. for several days and weighed. Based on the results, the water content of each plant exposed to the stress was determined.

TABLE 1

Salt stress treatment

|  | Dry weight/fresh weight | Ratio* | Water content (%) |
| --- | --- | --- | --- |
| control | 0.1505380 | 1.000 | 84.92 |
| individual No. 1 | 0.1287313 | 0.854 | 87.12 |
| individual No. 2 | 0.1215596 | 0.808 | 87.84 |

*The relative dry weight/fresh weight ratio of each transformant calculated when the dry weight/fresh weight ratio of the control plant is taken as 1.

TABLE 2

Dry stress treatment

|  | Dry weight/fresh weight | Ratio* | Water content (%) |
| --- | --- | --- | --- |
| control | 0.1602564 | 1.000 | 83.97 |
| individual No. 1 | 0.1274725 | 0.795 | 87.25 |
| individual No. 2 | 0.1349073 | 0.842 | 86.51 |

*The same meaning as the one indicated in Table 1.

Plants having a greater ability to retain water or a greater efficiency to utilize water and more tolerant of drought (e.g., refer to Lincoln Taiz and Eduardo Zeiger, Plant Physiology, Chapter 14 Stress Physiology, The Benjamin/Cummings Publishing Company, Inc.). Further, it is known that the ability to retain water content is an issue of importance for creatures in general which live in dry or high salt areas (e.g., refer to Kent F. McCue et al., TIBTECH-December 8, 358–362). Prior attempts to solve the problem have focused on a method wherein plants were allowed to accumulate an osmoprotectant in their body to enhance a water retaining ability, whereby making them tolerant to both salt and drought stress (Kent F. McCue et al., ibid). One such attempt includes the introduction of trehalose synthase gene into a plant.

In contrast, the present invention is unique in that water-retaining capability of a plant is improved by a substantially different approach, i.e., by means of WCH protein gene. It is expected that plants which acquire an improved water-retaining ability in accordance with the method of the invention will be more tolerant to salt stress and drought stress.

EXAMPLE 5

Isolation of the gene of plasma membrane-located WCH protein from *Nicotiana tabacum*

A total RNA fraction was extracted from a leaf tissue specimen of *Nicotiana tabacum* in accordance with the method of Ostrem et al. [Plant Physiology 84, 1270–1275 (1987)], with modifications made as follows:

1) The plant was ground and shaken on ice for 1 hour together with the extraction buffer and phenol.

2) After centrifugation, the supernatant was shaken for 1 hour with chloroform on ice.

poly(A)$^+$RNA was purified by using QuickPrep mRNA purification Kit (purchased from Pharmacia) in accordance with the manufacturer's instructions.

To isolate the cDNA encoding the WCH protein, primers were prepared by a DNA synthesizer (manufactured by Applied Biosystems) by reference to the nucleotide sequence (SEQ ID NO:1) of the WCH protein cDNA derived from *Mesembryanthemum crystallinum* described in Example 1. The sequences of the primers were as follows:

Primer 1: GAAGATCTATGATCTTTGCCCTTGTT-TACTGC. (SEQ ID NO:4)

Primer 2: GTCAGATCTAGCACGCGACTTGAATG-GAATAGCC. (SEQ ID NO:5)

The cDNA template used in the reverse transcription polymerase chain reaction (RT-PCR) was synthesized by StrataScript™ RT-PCR+Kit; (purchased from STRATAGENE) by employing 50 ng of poly(A)$^+$RNA extracted and purified from *Nicotiana tabacum* and the oligo dT primer in accordance with the manufacturer's instructions.

The RT-PCR was performed by using the above-mentioned cDNA template, 20 pmole of the above-mentioned primers 1 and 2, 200 mmol each of dATP, dGTP, dCTP and dTTP, 1×PCR buffer (purchased from Takara Shuzo Co., Ltd.) and 2.5 U of AmpliTaq DNA polymerase (purchased from Takara Shuzo Co., Ltd.) (in a total reaction volume of 100 ml. The reaction was performed for 32 cycles, the cycle consisting of 1 minute at 91° C., 1 minute at 42° C. and 2 minutes at 72° C. The PCR product was separated on a 1% agarose gel and stained with ethidium bromide. Thus the product was detected at the position of about 550 bp.

The PCR fragment was recovered from the gel and subcloned into plasmid pCRII by using TA Cloning Kit (purchased from Invitrogen) in accordance with the manufacturer's instructions.

The nucleotide sequence of the resulted PCR fragment was identified by DNA Sequencer Model 373A (manufactured by Applied Biosystems). The reaction was performed by using Taq Dye Terminator Cycle Sequencing Kit (purchased from Applied Biosystems) in accordance with the manufacturer's guidance. In this Example, a partial cDNA fragment of the gene of the plasma membrane-located WCH protein having the nucleotide sequence shown in SEQ ID NO: 3 was obtained.

EXAMPLE 6

Construction of gene for the transformation of *Nicotiana tabacum*

By using the gene fragment obtained in Example 5, an antisense gene to be introduced into *Nicotiana tabacum* was constructed. The PCR fragment subcloned into the plasmid pCRII was digested with restriction enzymes SacI and XbaI and purified. This fragment was inserted into plasmid pBI121 at the site formed by digestion with SacI and XbaI. Thus the gene construct pA121 was obtained.

EXAMPLE 7

Transformation of *Nicotiana tabacum*

*Nicotiana tabacum* was transformed with pA121 by substantially the same method as the one described in Example 3.

In accordance with the present invention, which provides a method for controlling the water content of a plant by way of the introduction therein a gene which encodes a plant water channel protein, the water content of the plant can be controlled and hence, the plant is made tolerant to water-related stress without any disadvantages from the viewpoint of energy due to the consumption of carbon fixed by photosynthesis or problems due to the accumulation of saccharides which may exert unpredictable effects on the qualities of products and the metabolic system of the plant.

---

What is claimed is:

1. A method for controlling the water content of a plant; comprising,
transforming said plant with a gene encoding a plant water channel protein, wherein said gene is operatively introduced into the plant.

2. A method according to claim 1 for controlling the water content of a plant wherein said gene encodes a plant water channel protein of the type located in plasma membrane.

3. A method according to claim 1 or 2 for controlling the water content of a plant wherein said plant water channel protein gene is introduced into the plant in such a manner that the genetic code sill be translated in the sense direction.

4. A method according to claim 3 for controlling the water content of a plant wherein said plant water channel protein gene is derived from a plant which is tolerant to salt stress or drought stress.

5. A method for controlling the water content of a plant; comprising,
transforming said plant with a gene encoding a plant water channel protein derived from *Mesembryanthemum crystallinum*, wherein said gene is operatively introduced into the plant.

6. A plant which has a gene encoding a plant water channel protein, wherein said gene has been operatively introduced into said plant so that the plant will have a greater water content than the original plant which does not have said gene when these plants are grown under the same condition.

7. A plant as claimed in claim 6, wherein said gene encodes a plant water channel protein of the type located in plasma membrane.

8. A plant as claimed in claim 6 or 7, wherein said plant water channel protein gene has been introduced into the plant in such a manner that the genetic code will be translated in the sense direction.

9. A plant as claimed in claim 8, wherein said plant water channel protein gene is derived from a plant which is tolerant to salt stress or drought stress.

10. A plant as claimed in claim 9, wherein said plant water channel protein gene is derived from *Mesembryanthemum crystallinum*.

11. A plant as claimed in claim 10 selected from the group consisting of soy bean, maize, potato, tomato and tobacco.

12. A method for controlling the water content of a plant, which comprises:
introducing into a plant water channel protein gene from *Mesembryanthemum crystallinum* to produce a transgenic plant, wherein said plant has a greater water content than the original plant which does not have said gene when the original plant is grown under the same conditions.

13. The method of claim 12, wherein said plant is *Nicotiana tabacum*.

14. A transgenic plant which has a plant water channel protein gene from *Mesembryanthemum crystallinum* introduced therein, wherein said plant has either a greater or smaller water content than the original plant which does not have said gene when the original plant is grown under the same conditions.

15. The plant of claim 14, wherein said gene is a heterologous gene.

16. The plant of claim 15, wherein said plant is *Nicotiana tabacum*.

17. The plant of claim 16, wherein said gene encodes a plant water channel protein of the type located in plasma membrane.

18. The plant of claim 16, wherein said plant water channel protein gene has been introduced into the plant in such a manner that the genetic code will be translated in the sense direction.

19. A plant as claimed in claim 16, wherein said plant water channel protein is derived from a plant which is tolerant to salt stress or drought stress.

20. A plant as claimed in claim 14 selected from the group consisting of soy bean, maize, potato, tomato and tobacco.

21. The method according to claim 1, wherein said gene encoding said water channel protein is from pea, *Arabidopsis thaliana*, tomato, *Mesembryanthemum crystallinum*, corn, rice, kohlrabi, soybean or barley.

22. The plant according to claim 6 wherein said gene encoding said water channel protein is from pea, *Arabidopsis thaliana*, tomato, *Mesembryanthemum crystallinum*, corn, rice, kohlrabi, soybean or barley.

23. The plant according to claim 6 wherein said gene encoding said water channel protein is from *Pisum sativum*.

24. The plant according to claim 6 wherein said gene encoding said water channel protein is from *Arabidopsis thaliana*.

25. The plant according to claim 6 wherein said gene encoding said water channel protein is from Tomato.

26. A method for controlling the water content of a plant, comprising:

growing a plant containing a gene encoding a plant water channel protein under conditions which allow said plant to take up more water than a corresponding plant which does not have said gene and has been grown under identical conditions, wherein said gene is operatively introduced into the plant.

27. A method according to claim 26, wherein said gene encoding said water channel protein is from pea, *Arabidopsis thaliana*, tomato, *Mesembryanthemum crystallinum*, corn, rice, kohlrabi, soybean or barley.

* * * * *